United States Patent [19]

Wesseling

[11] Patent Number: 5,400,793
[45] Date of Patent: Mar. 28, 1995

[54] METHOD OF DETERMINING THE STROKE VOLUME AND THE CARDIAC OUTPUT OF THE HUMAN HEART

[75] Inventor: Karel H. Wesseling, The Hague, Netherlands

[73] Assignee: Nederlandse Organisatie Voor Toegepast-Natuurwetenschappelijk Onderzoek Tno, Delft, Netherlands

[21] Appl. No.: 94,052

[22] PCT Filed: Jan. 28, 1992

[86] PCT No.: PCT/NL92/00022

§ 371 Date: Sep. 20, 1993

§ 102(e) Date: Sep. 20, 1993

[87] PCT Pub. No.: WO92/12669

PCT Pub. Date: Aug. 6, 1992

[30] Foreign Application Priority Data

Jan. 29, 1991 [NL] Netherlands .................. 9100150

[51] Int. Cl.⁶ .............................................. A61B 5/029
[52] U.S. Cl. ...................................... 128/672; 128/691; 128/692; 128/713
[58] Field of Search .................... 128/691–694, 128/713, 668, 672, 736

[56] References Cited

U.S. PATENT DOCUMENTS

| | | | |
|---|---|---|---|
| 4,632,125 | 12/1986 | Webler et al. | 128/692 |
| 4,841,981 | 6/1989 | Tanabe et al. | 128/692 |
| 5,183,051 | 2/1993 | Kraidin et al. | 128/687 |
| 5,211,177 | 5/1993 | Chesney et al. | 128/713 X |

OTHER PUBLICATIONS

"The Static Elastic Properties . . . ", Langewouters et al. pp. 425–435, 1984.
"Use of a Simulation Model For . . . ", Brubakk, pp. 697–706, Nov. 1978.
"Estimation of Beat-to-beat stroke . . . ", DeLoskey et al. pp. 707–714, 1978.
"Ecoulements pulses dans les . . . ", Flaud et al., pp. 869–882, Nov., 1974.
"Beat-by-Beat Stroke Volumn from . . . ", Guier et al., Jul. 1974.

*Primary Examiner*—Angela D. Sykes
*Attorney, Agent, or Firm*—Bachman & LaPointe

[57] ABSTRACT

Method of determining the stroke volume of the human heart from the pulse-type blood-stream pressure signal derived from the aorta and consisting in each case of a systolic and a diastolic period. The method comprises calculating the flow q(t) from the pressure p(t) and integrating the flow over the systolic period, the aorta being regarded as a transmission line supplemented with a windkessel compliance and the pressure/volume relationship in the aorta as an arctangent relationship. The pressure represented by the pressure signal—for each stroke prior to the calculation of the flow—is linearized by the arctangent relationship, for fixed aorta length, or the aorta pressure/cross section, the values, associated with the final diastolic pressure, of the characteristic impedance of the transmission line and windkessel compliance being adhered to or is used without modification. The characteristic impedance of the transmission line and the windkessel compliance are continuously adapted to the pressure of the windkessel compliance for each stroke concerned. Additionally, to calculate the flow, the flow through the peripheral resistance is added.

9 Claims, 6 Drawing Sheets

METHOD OF DETERMINING THE STROKE VOLUME AND THE CARDIAC OUTPUT OF THE HUMAN HEART

BACKGROUND OF THE INVENTION

The invention relates to a method of determining the stroke volume and the cardiac output of the human heart from the pulse-type bloodstream pressure signal derived from the aorta and consisting in each case of a systolic and diastolic period. It is known in practice to calculate the stroke volume and the cardiac output with the aid of a thermodilution determination by injecting cold liquid into the blood stream and measuring it downstream at regular intervals.

In another known method, a pulse contour method or prescription is used to determine the stroke volume $V_s$ and the cardiac output or heart minute volume Q from a pressure signal p(t) measured in the human aorta. In this connection, the stroke volume is the volume of blood ejected by the heart in one contraction or stroke. A typical value is, for example, 70 cm$^3$, but this quantity can vary from stroke to stroke. The cardiac output is the volume of blood which the heart pumps in a unit time of one minute. In this connection, a typical value is 5 l/min, and this volume can typically vary between 2 and 30 l/min.

In the past relatively simple relationships have been assumed between the measured aorta pressure signal p(t) and the mean aorta flow q(t). In this connection, the starting point is the pressure signal since said pressure can be measured relatively easily and well, but the flow cannot. In practice it has been found that such a relationship or "model" is much more complicated than was first assumed. This has emerged, in particular, in hospitals, where this so-called pulse contour calculation has resulted in frustration in the case of seriously ill patients.

Figure 1A:
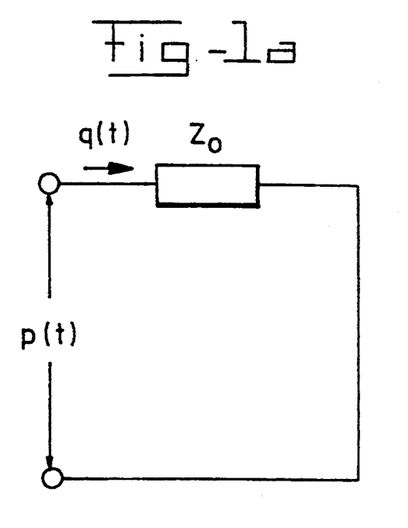
FIGS. 1a and 1b show the two known pulse contour models, viz. the windkessel model and the uniform transmission line model.
Figure 1B:
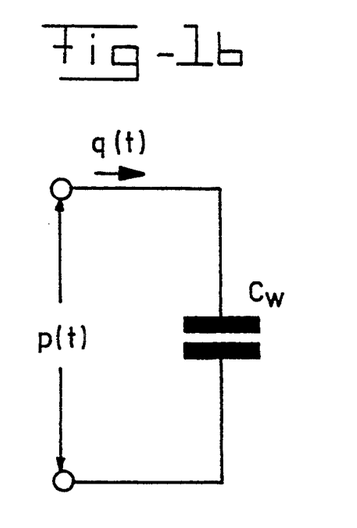

In practice, usually a so-called "Windkessel" or air-receiver model is assumed, the aorta being conceived as a single compliance (FIG. 1b). In this case a windkessel—a container partially filled with liquid and with gas—which can absorb the surges in flow and buffer them in the gas bubble and which is incorporated downstream of a pulsatile pump is meant. The volume of blood ejected by the heart pump is largely received in the aorta or windkessel and partially flows away through the peripheral vascular regions of the various organs which branch off from the aorta. In the period in which the heart pump does not eject a volume of blood, i.e. the diastolic period $T_d$, the outward flow from the windkessel continues to be fed to the peripheral vascular regions. The aorta does not then contain any gas but the aorta wall is elastic and this elastic vascular wall fulfils the same function as the windkessel.

This concept contains various factors which are neglected. Firstly, the aorta is much longer than wide. In fact, the pressure wave generated by the heart requires a time of 0.1 to 0.3 sec. to reach the end of the aorta and then approximately the same time to return to the heart, whereas the entire expulsion period of the heart (the systolic period or systole, $T_s$) lasts only 0.2 to 0.4 sec. At the beginning of the output flow, only a small portion of the compliance is therefore available for buffering the outward flow. However, still more important is the fact that, after two times the propagation or transit time of the pressure wave, twice the capacity is available, albeit with a doubling of the initial pressure wave amplitude.

In addition, a second neglect which is generally made is that the windkessel is linear, that is to say a doubling of the stored stroke volume is accompanied by a doubling of the pressure. In reality it has been known for a number of years from the work of G. J. Langewouters et al. in *J. Biomechanics* 17, pages 425–435 (1984) that the relationship between pressure p and volume V is strongly nonlinear in accordance with an arctangent function (FIG. 3a). In addition, said arctangent function is dependent on the age and sex of the patient. Finally, the drainage from the aorta to the peripheral vascular zones is not concentrated at one location but distributed along the aorta. That is to say, it takes a little time before the increased pressure at the start of the aorta has reached the various branching points to the peripheral vascular zones and the drainage actually increases due to the increased aorta pressure.

To summarise, the neglects therefore amount to the fact that the aorta does not behave linearly and that there is a time factor due to a travelling wave along the aorta.

In practice, however, another model is also assumed, the so-called transmission line model (FIG. 1a). In this approximation, the aorta is conceived as a homogeneous elastic tube of "adequate" length filled with liquid (blood), with drainage to the peripheral vascular zones concentrated at the end. Such a tube has two characteristic properties. A pressure wave generated by the heart at the start of the tube travels at finite velocity $v_p$ to the end of the tube is partially reflected there and travels back to the start of the tube. By the time the reflected wave arrives there, the expulsion phase, the systole, of the heart is already over, the aorta valve is already closed and the heart no longer has any trouble from the reflected wave since the latter is, after all, held back by the closed valve. The "adequate length" is that length of tube which, given the propagation velocity of the wave, ensures that the reflected pressure wave does not return too soon. The propagation velocity $v_p$ is primarily determined by the area A of the cross section of the aorta, the compliance C' of the aorta per unit of length and the density $\rho$ of the blood in the tube as follows:

$$V_p = \sqrt{A/\rho C'}.$$

In addition to the propagation velocity the second characterising property is the characteristic impedance $Z_0$. This impedance reflects the ratio between the amplitude of the pressure wave and that of the accompanying flow wave in the aorta and is also affected by the cross sectional area A and the compliance C'. In fact, the characteristic impedance is given by the formula:

$$Z_o = \sqrt{\rho/(AC')}.$$

The fact that the ratio between pressure p(t) and flow q(t) is fixed and given by the formula: $q(t)=p(t)/Z_0$ means that the pressure wave and the flow wave at the start of the aorta are identical in shape at least till the instant that the reflected pressure (and flow) wave has (have) returned.

This model also contains various approximations which, although they have less serious consequences for the stroke volume calculation, make the latter still too inaccurate under certain circumstances. Firstly, it is also true of this model that the aorta does not behave linearly in relation to the relationship between pressure p and volume V and therefore, with constant aorta length, as regards the cross section $A=V/1$. Since the compliance $C'$ per unit of length is the derivative of the area of the cross section with respect to pressure, at the prevailing pressure $p_0$: $C'=[dA/dp]p_0$, A will indeed increase with increasing pressure, but at the same time $C'$ will decrease because the aorta becomes increasingly less distensible with increasing pressure in accordance with the arctangent function mentioned (FIG. 3b). In a particular pressure region, these two factors will compensate for each other in the formula for $Z_0$ and the latter will be virtually constant. At increasingly higher pressures, the decrease in $C'$ takes place more quickly than the increase in A, and the characteristic impedance $Z_0$ will start to slowly increase in accordance with the root of the inverse product of A and $C'$. The nonlinearity therefore plays a role but this is less serious than in the windkessel model. A second approximation is that the aorta is assumed to be homogeneous. In reality, the aorta is neither homogeneous in cross section nor in distensibility of the vascular wall. The aorta cross section decreases towards the periphery. This is initially compensated for because the arterial branches of the aorta start to contribute to the total cross section as soon as the pressure wave and flow wave reach the branches. In addition, the vascular wall is, however, increasingly less distensible towards the periphery. This manifests itself in a decrease in compliance $C'$. Since both A and $C'$ in the formula for the characteristic impedance decrease over the aorta towards the periphery, $Z_0$ will increase. This means that there is no question of a single reflection at the peripheral resistance at the end of the aorta tube, as assumed in the model, but that there are distributed reflections along the entire aorta, initially small but considerably increasing later in the systole. With a short systolic period, the heart only experiences the (low) impedance at the start of the aorta while contracting, but with a longer-lasting systole it also experiences the (higher) peripheral impedance. This will mean that the instantaneously expelled quantity of blood will become increasingly smaller as the systole advances since it is gradually curbed by the increasing reflected impedance.

A third approximation is the following. After the blood has been forced into the aorta due to an increase in the pressure, the pressure in the subsequent diastolic period will, of course, not be zero immediately, but the aorta will slowly empty through the peripheral resistance. As a consequence of this, the subsequent stroke will be forced out against a somewhat increased pressure and the two pressures will in fact be superimposed on each other. The diastolic pressure will always increase further with every stroke until equilibrium has been reached between systolic inward flow and diastolic outward flow. This is comparable to a windkessel function.

Finally, it is also true that the drainage is not concentrated at the end of the aorta but is distributed over the length thereof.

To summarise, the neglects are a consequence of the fact that the aorta has nonlinear properties and cannot be conceived as homogeneous.

Both the above model concepts are not adequate if an attempt is made to calculate the aorta flow pattern from the aorta pressure as a function of time during a systole using the models. The curve found with the transmission line model only resembles an actual flow curve to any extent under the conditions of a short-duration systole. The windkessel model does not actually even permit a calculation of a flow curve. In practice, for both models only the stroke volume of the heart, that is to say the flow curve integrated over one systole, is therefore calculated from the pressure curve.

SUMMARY OF THE INVENTION

The object of the invention is to eliminate the abovementioned problems and to provide a method for the said determination of the stroke volume and cardiac output which takes account both of the windkessel properties and the transmission-line properties. This is achieved in a method, of the type mentioned at the outset, by calculating the flow $q(t)$ from the pressure $p(t)$ and integrating the flow over the systolic period, the aorta being regarded as a transmission line supplemented with a windkessel compliance and the pressure/volume relationship in the aorta as an arctangent relationship. In this case, the nonlinear aorta properties are important and are involved in this method, while it is advantageous for the verification of the correctness of the steps of the method if the flow curve can be continuously calculated and displayed during a systole. The integral of the flow curve then yields the stroke volume.

BRIEF DESCRIPTION OF THE DRAWINGS

The invention will be explained in greater detail on the basis of an embodiment, reference being made to the drawings, wherein:

FIG. 3a shows a graph with stylised pressure/cross section and pressure/compliance per unit length relationship for a 40 year old male aorta;

FIG. 3b shows a diagrammatic representation of the calculation of a linearised pressure using the arterial final diastolic pressure as initial value;

DETAILED DESCRIPTION

Figure 2A:
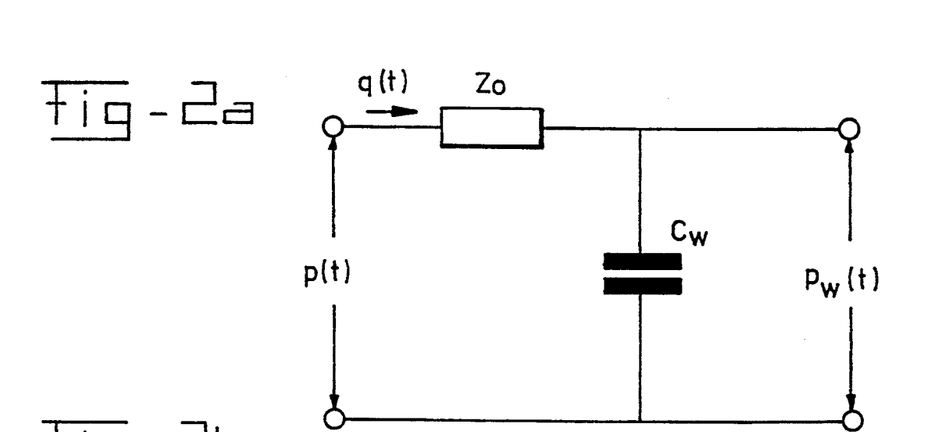
FIGS. 2a and 2b show the pulse contour model according to the invention based on the transmission line model supplemented by the windkessel function, respectively without and with peripheral drainage.

The invention assumes the transmission-line model, in particular, the transmission-line property that pressure wave and flow wave are related by a fixed factor, the characteristic impedance $Z_0$, at least before reflections return to the heart from the periphery. This model lacks the gradual curbing of the outward flow from the heart by early reflections and the diastolic windkessel action. According to the invention, these two shortcomings are eliminated by means of adding one component, an aorta windkessel compliance $C_w$, to the transmission-line model (see FIG. 2a). After all, in the systole, the flow is determined in the first instance by $Z_0$ and is then gradually curbed during the ejection phase by the pressure increase of $p_w(t)$ which is built up in the windkessel receiver by the inflow $q(t)$.

A further neglect was that the peripheral drainage was conceived as concentrated at the end of the transmission line. As a result of now associating, according to the invention, the equivalent peripheral resistance $R_p$ with the windkessel compliance $C_w$, the latter is connected to an average (albeit low-pass-filtered) pressure and consequently represents reality better. See FIG. 2b. For in this model, the outward flow $q_{rp}(t)$ is subtracted from the inflow q(t) so that the curbing of the inflow takes place somewhat less rapidly.

The improved model according to the invention contains linear time-invariant components. In reality, we are concerned with a strong nonlinear aorta whose pressure/cross section relationship varies in accordance with an arctangent. According to the invention two versions are now possible. In the first version, the pressure curve recorded in the method is first linearised and then applied to a linear pulse contour model. In the second version, the pressure measured in the method is regarded as given, but the pulse contour model is provided with pressure-dependent components.

The Linearised Pressure Curve Model

In this first version it i assumed that the pressure curve arises because a certain volume of blood is pumped by the heart into the aorta, and this is followed by a rise in pressure. The magnitude of the rise in pressure depends on the pressure/volume relationship of the aorta. At a high pressure, a low volume increase will result in a high pressure increase, whereas at a low pressure, the same volume increase results in a smaller pressure increase (arctangent relationship). However, it is possible to calculate, by means of the pressure/volume relationship assumed to be known, the pressure curve which would have existed if the aorta had had a linear pressure/volume relationship. The procedure can be indicated graphically in a simple manner (see FIG. 3b). For every stroke, the start of the expulsion phase in the pressure curve and the associated final diastolic pressure $p_d$ are determined. At said pressure, the nonlinear aorta pressure/volume relationship or, assuming a fixed aorta length, pressure/cross section relationship is linearised by means of the tangent to the curve and the equivalent linear pressure is calculated for every pressure sample ten on the pressure curve. Assuming an initial pressure $p_d$ of 70 mmHg, in this example of a pressure sample of 100 mmHg, the equivalent linear pressure becomes equal to approximately 92 mmHg. This pressure is then applied to the pulse contour model which, for characteristic impedance and windkessel compliance calculated from the applicable pressure/cross section relationship, has the values associated with the final diastolic pressure for the stroke concerned.

The Nonlinear Model

In this second version, it is assumed that the pressure curve arises as a result of the outward flow of the blood into a nonlinear aorta, given all its properties and not only its windkessel properties, as above. A linear correction is not then applied to the pressure curve but is accepted as it is. However, during the expulsion phase of the stroke concerned, the value of the characteristic impedance and of the windkessel compliance varies according to the pressure value such as it exists at any instant and is calculated from the nonlinear arctangent pressure/cross section relationship according to the above formulae. At any instant when a pressure sample is then, the associated characteristic impedance and windkessel compliance, and the effect of these altered values on the flow are calculated.

The Use of the Arctangent Relationship

According to Langewouters et al., the relationship between the area of the aorta cross section and the aorta pressure can be specified using the formula:

$$A(p) = A_m[0.5 + (1/\pi)\tan^{-1}\{(p-p_0)/p_1\}] \quad (1)$$

where A(p) is the cross section as a function of the pressure p, $A_m$ is the limit cross section at very high pressure, and $p_0$ and $p_1$ are, respectively, the pressure at the point of inflection of the relationship and the slope of the relationship at the point of inflection. For a typical curve see FIG. 3a.

The compliance C' per unit of length as a function of the pressure follows from this as a result of differentiation with respect to p as:

$$C(p) = [dA/dp]_{p0} = C_m/\{1 + (p-p_0)^2/p_1^2\} \quad (2)$$

where $C_m = A_m/\pi p_1$ = the maximum compliance at $p = p_0$. The values of the parameters $A_m$, $p_0$ and $p_1$ are known from the work of Langewouters et al. In particular, these parameters depend on the sex and age of the person. The value for $A_m$ has, in addition, a dispersion of approximately 20%. It is not therefore possible to determine the values of the components in the pulse contour model in an absolute sense without more exact calibration unless a standard deviation of approximately 20% is regarded as acceptable.

$Z_0$ and $v_p$ can readily be calculated with the aid of A and C' found in this way. To calculate the total windkessel compliance of the aorta, still one more parameter is required, namely the effective length of the aorta. The windkessel compliance is then the compliance per unit of length multiplied by the effective length: $C_w = C'\ell$. A good value for adults is 60 cm.

The Value of the Peripheral Resistance

Figure 2B:
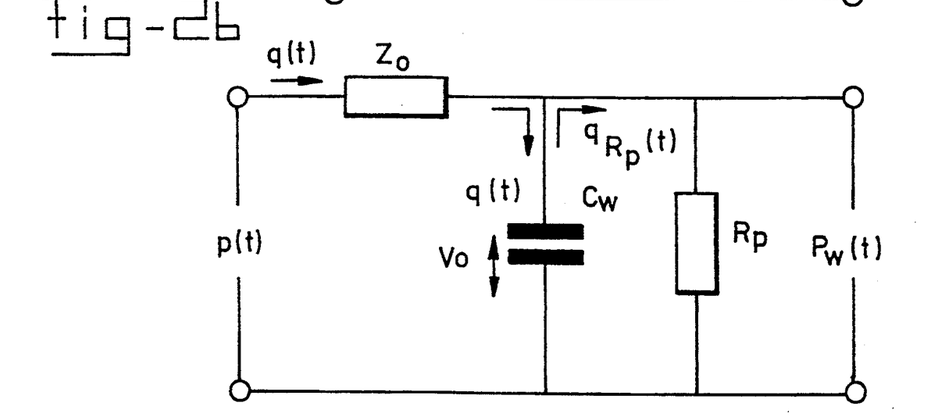

The pulse contour model of FIG. 2b includes a component representing the total peripheral resistance $R_p$ of all the vascular drainage beds in parallel. The value of the latter is initially unknown. After the stroke volume $V_s$ has been calculated for the first time and the heartbeat rate f, the number of heartbeats per minute, has been found from the sum of the systolic and diastolic time periods $T = T_s + T_d$, if $f = 60/T$, the cardiac output can be calculated as the product of the heartbeat rate and the stroke volume for the stroke concerned:

$$Q = fV_s. \quad (3)$$

The average aorta pressure $p_m$ is also known as the integral of the pressure over a time period divided by the time period:

$$p_m = (1/T) \cdot \int_T p(t) dt \quad (4)$$

$$R_p = p_m/Q \quad (5)$$

Since the peripheral resistance only varies slowly, its value, calculated for the present stroke, can be used for the flow calculation of the subsequent stroke. For the first stroke, a reasonable initial estimate will have to be taken. Since the value of the flow in the systole is not strongly dependent on the value of the peripheral resistance, a rapid convergence is obtained in this way.

Calculation of the Flow Using the Pulse Contour Model

The flow q at any instant can be calculated using a simulation. In this connection, equations are set up which describe the behaviour of the model of FIG. 2b. The aorta flow follows from the equation:

$$q(t) = 1/Z_o \cdot \{(p(t) - p_w(t)\}.$$

The flow through the peripheral resistance follows from: $q_R(t) = p_w/R_p$; and the volume in the air-receiver compliance $C_w$ follows from: $V_w(t) = V_o + f\{(q(t) - q_R(t)\}dt$, where $V_o$ is the initial volume in $C_w$. Finally, the pressure in the air-receiver follows from the volume/pressure relationship $p_w(t) = f(V_w(t))$.

As stated earlier, the stroke volume $V_s$ can be found from the flow curve by integrating the flow during the systole, the heartbeat rate $f$ as the quotient of 60 and the time period of every stroke, the cardiac output Q as the product of stroke volume $V_s$ and heartbeat rate $f$, and the peripheral resistance $R_p$ as the low-pass-filtered quotient of the average pressure $p_m$ and the cardiac output Q as indicated in formulae 3, 4 and 5.

Figure 4A:
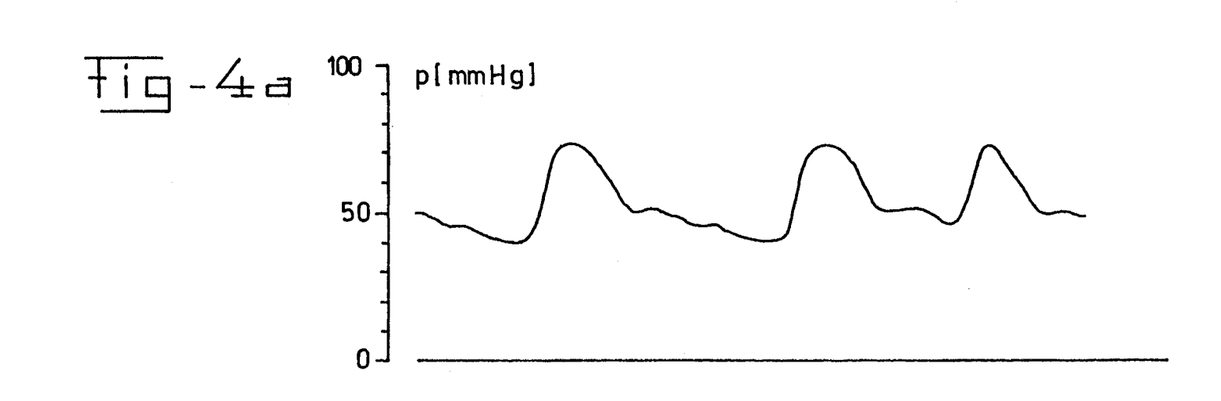
FIGS. 4a and 4b show, respectively, an input pressure signal $p(t)$ and a calculated flow curve $q(t)$ calculated with the aid of a pulse contour model.
Figure 4B:
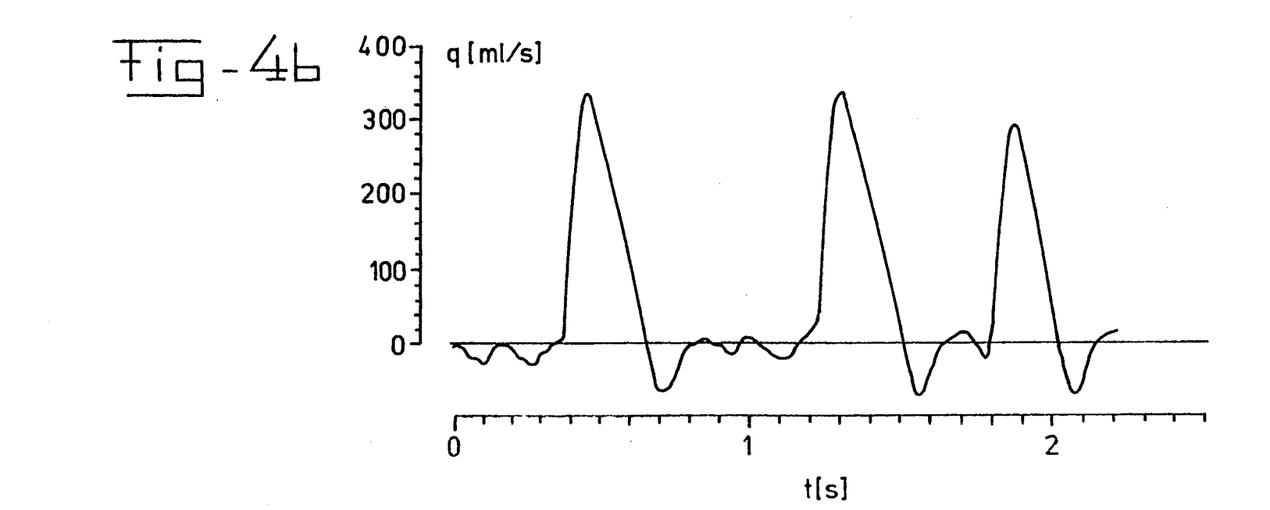
Figure 5A:
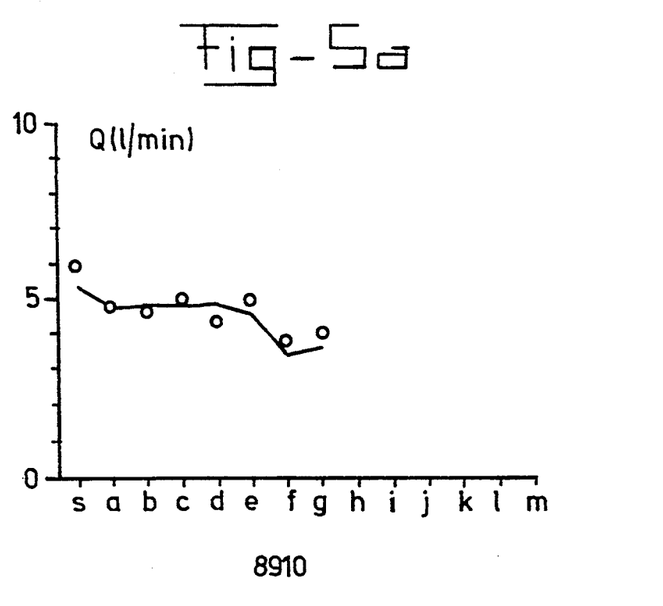
FIG. 5 shows a number of graphs of the pulse contour (line) and thermodilution (o) cardiac output of six open-heart operation patients plotted against the number of the thermodilution determination.
Figure 5B:
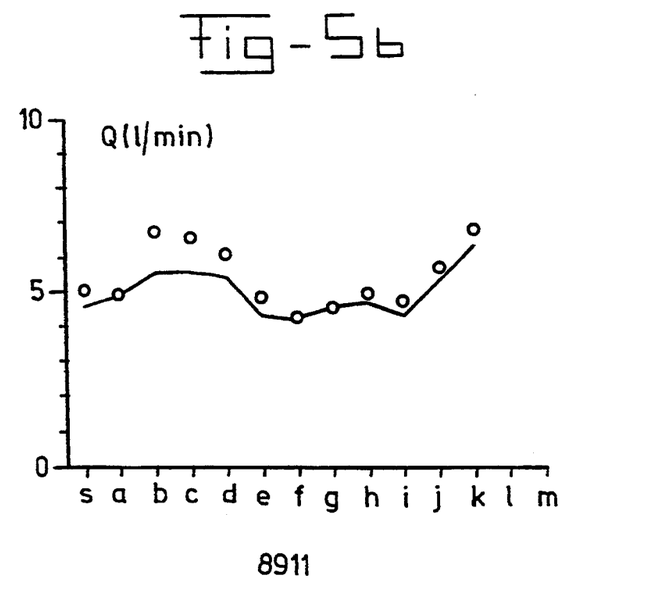
Figure 5C:
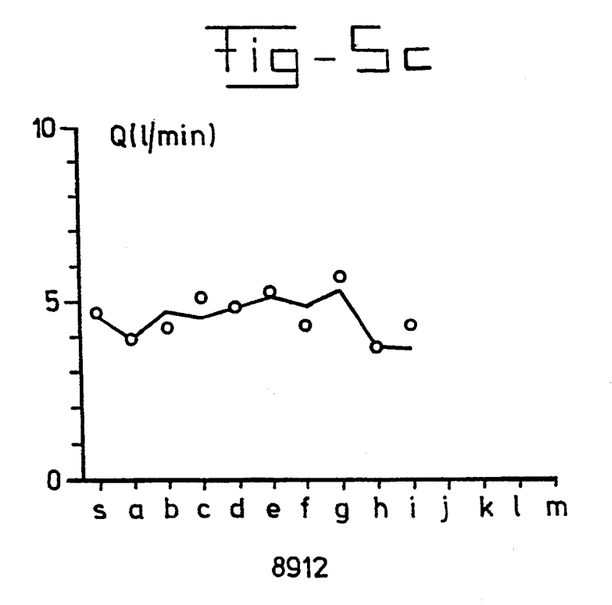
Figure 5D:
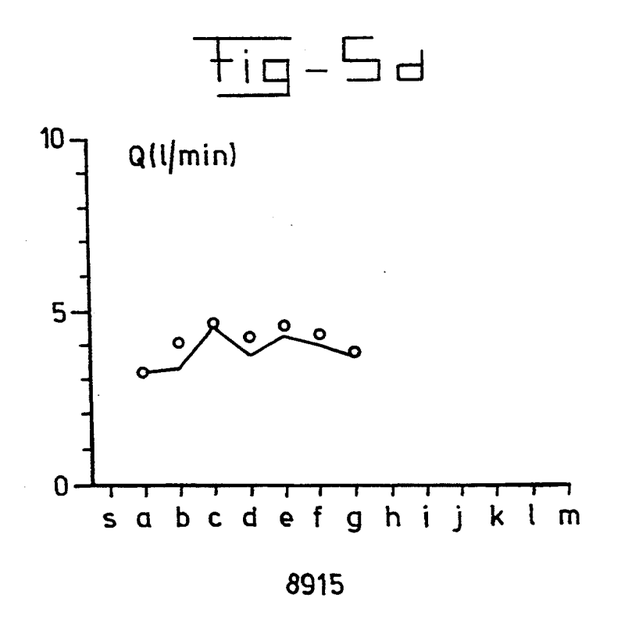
Figure 5E:
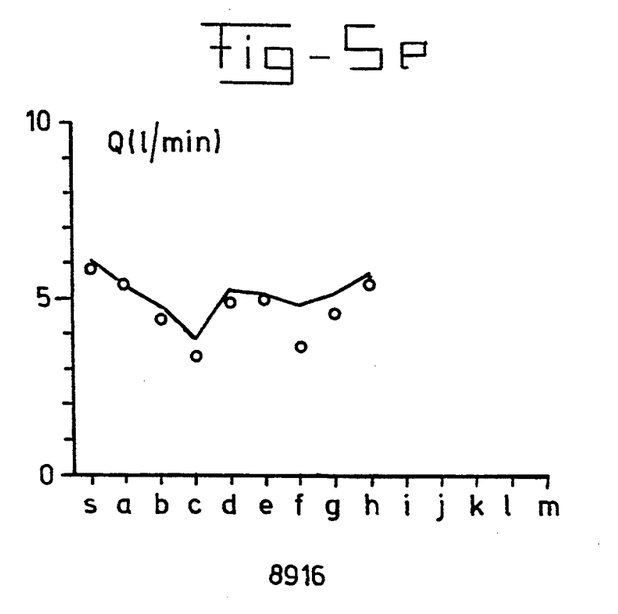
Figure 5F:
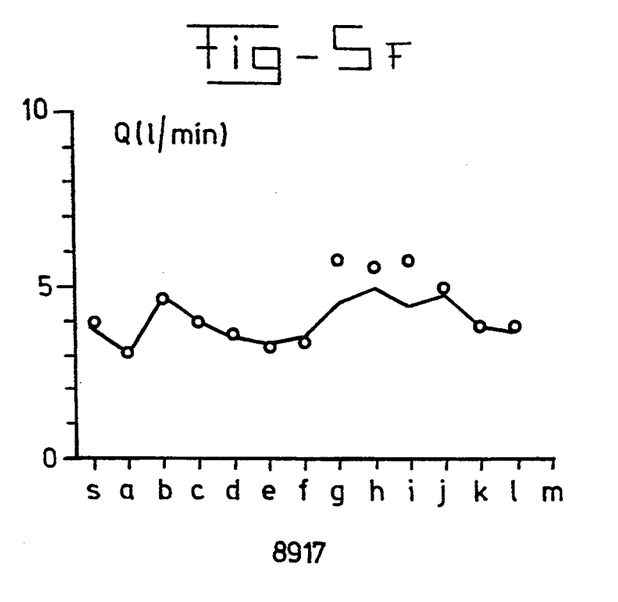

A measured pressure curve and the flow curve calculated from it are shown in FIG. 4 for a 62 year old male patient. Before every stroke, the beginning of the rising edge of the pressure curve in FIG. 4a is determined using a pattern recognition algorithm. At this instant, the diastolic pressure $p_d$ on the curve is recorded, and with the latter, the correct values for the characteristic impedance and the windkessel compliance are found using a function generator and introduced into the model. The pressure is linearised using the arctangent pressure/cross section relationship and is applied to the model. The correct values for the parameters which determine the arctangent pressure/cross section relationship follow from regression equations according to Langewouters et al. and are as follows for women and men, respectively, having an age n:

| for women: | for men: |
|---|---|
| $A_m = 4.12$ | $A_m = 5.62$ |
| $p_o = 72 - 0.89n$ | $p_o = 76 - 0.89n$ |
| $p_l = 57 - 0.44n$ | $p_l = 57 - 0.44n$ | where $A_m$ is in cm$^2$, the pressures p is in mmHg and the age n is in years.

Obviously, these calculations can advantageously be carried out by a digital processor. For this purpose, it is necessary to replace the continuous pressure curve by a series of samples with regular spacing intervals and to repeat the calculation for every sample taken. The flow curve therefore becomes available at these time instants. A preferred sample interval is 10 ms. A shorter interval of 5 ms is possible if a fast computer is used but only gives a marginal improvement in the precision. The integration of the flow curve in order to calculate the stroke volume is replaced by a summation of the flow samples in the systolic period.

The Precision of the New Method

The new method has been evaluated in six patients who were undergoing an open-heart operation. The reference value for the cardiac output was measured at some time instants during the operation by repeating a thermodilution (TD) determination at least four times after injections of cold liquid distributed with precise regularity over the respiratory cycle. A single thermodilution determination would be too inaccurate. The particular feature is that the four determinations were injected so as to be spread regularly over the respiratory cycle, as a result of which an averaging of the four values usually means an improvement in the precision of the estimate of the actual cardiac output by a factor of four. This improvement is only achieved with mechanical insufflation and not, therefore, if the patient breathes spontaneously. Spontaneous breathing always takes place during the first determination, i.e. at "s", as marked in FIG. 5, and during all the subsequent determinations, the patient is anaesthetised and he is artificially insufflated.

The cardiac output calculated by the novel pulse contour method was recorded at the same time for comparison. The results are shown separately for each of the patients in FIG. 5. The number of simultaneous determinations, the mean error, the error standard deviation (SD) and the error span are shown for each patient number 8910 to 8912 and 8915 to 8917 in table 1 and averaged for the group. Note that the sixth patient has a larger error for three determinations. These were carried out after a period of total heart-long bypass while, although the heart was already beating and pumping blood, the pump of the heart-lung machine was still assisting at approximately one liter per minute. This flow was in fact measured by the thermodilution method but not by the pulse contour method, resulting in this discrepancy.

For comparison, the cardiac output was also calculated by the earlier method according to Weaseling et al. from U.S. Pat. No. 3,841,313, which method was known as the most accurate in the literature. The mean error standard deviation was in this case 12%, against 8% for the novel method. The novel method therefore has a variance of less than half that of the old.

Roughly speaking, all the mean errors—shown in the last two rows—with the new method are more than a factor of $\sqrt{2}$ lower than with the older method.

TABLE 1

| pat nr | TD | PC old | PC new | Error old mean | Error old SD | Error old span | Error new mean | Error new SD | Error new span |
|---|---|---|---|---|---|---|---|---|---|
| 8910 | 4.67 | 5.21 | 4.53 | 0.54 | 0.43 | 1.02 | 0.14 | 0.38 | 1.12 |
| 8911 | 5.43 | 4.89 | 4.99 | 0.54 | 0.38 | 1.02 | 0.44 | 0.37 | 0.99 |
| 8912 | 4.59 | 5.31 | 5.41 | 0.73 | 0.45 | 1.24 | 0.08 | 0.38 | 1.37 |
| 8915 | 4.10 | 4.49 | 3.80 | 0.38 | 0.65 | 1.81 | 0.30 | 0.26 | 0.60 |
| 8916 | 4.69 | 4.98 | 5.13 | 0.29 | 0.45 | 1.44 | 0.43 | 0.33 | 0.89 |
| 8917 | 4.29 | 4.33 | 4.03 | 0.04 | 0.88 | 2.97 | 0.26 | 0.50 | 1.50 |
| mean | 4.63 | 4.87 | 4.50 | 0.24 | 0.54 | 1.58 | 0.13 | 0.37 | 1.08 |
| SD | 0.46 | 0.39 | 0.52 | 0.45 | 0.19 | 0.74 | 0.30 | 0.08 | 0.33 |

During the intensive monitoring of a patient in the operating theatre or intensive-care ward, it is only rarely possible to record the arterial pressure in the aorta. For reasons of convenience and safety for the patient, the pressure in the artery radialis or brachialis or a finger pressure will normally be recorded non-invasively. This pressure is distorted compared with the aorta pressure, that is to say the shape of the pressure curve has changed. This is due to the fact that the pressure curve generated in the aorta propagates through the arterial system to the more peripherally situated upper arm, pulse or finger and that this transmission path has certain properties, the most important of which are its narrow-band nature and its low-frequency resonance. It is possible to measure these properties in a large number of patients. In this connection, the inventor has found that the transmission properties have a relatively small spread around a mean value. In that case it is possible to correct the resonance properties by an anti-resonance in a filter, as a result of which it is indeed possible to accurately determine the pulse contour stroke volume of the left-hand half of the heart. To a good approximation, a simple second-order filter can be used for this purpose. In practice, a digital, IIR (infinite impulse response) second- or third-order filter is used which corrects the mean resonance precisely up to a frequency of 8 Hz.

In this case, on the basis of a series of input signal samples $x_n$, a series of output signal samples $y_n$ is calculated using the formula:

$$y_n = c_0 x_n + \sum_{k=1}^{M} d_k y_{n-k}$$

where c and d are constant, filter coefficients. For the second-order filter, the following values are used:

$c_0 = 0.077$ $d_1 = 1.484$ $d_2 = -0.561$

We claim:
1. A method for determining blood stroke volume from a pulsatile aorta blood-flow pressure signal in a subject, comprising the steps of:
   (a) providing a sensor means for measuring arterial blood pressure in a subject and obtaining a corresponding aorta blood-flow pressure signal consisting of a systolic and a diastolic period;
   (b) preparing a simulation model of the aorta as a transmission line supplemented with a windkessel compliance including an arctangent relation for the non-linear pressure-volume relation in the aorta;
   (c) calculating the flow of blood in the aorta as a function of time from the aorta blood-flow pressure signal employing the simulation model; and
   (d) determining the blood stroke volume from the flow of blood in the aorta over the systolic period.
2. A method according to claim 1 including deriving the arctangent pressure-volume relation with a fixed aorta length, from the aorta pressure/cross section according to the following expression:

$A(p) = A_m[0.5 + (1/\pi) \cdot \tan^{-1}\{(p-p_0)/p_1\}]$, where $A(p)$ = the cross section as a function of the pressure p,
$A_m$ = the limit cross section at very high pressure,
$p_0$ = the pressure of the point of inflection of the arctangent relationship, and
$p_1$ = is the slope of the arctangent relationship at the point of inflection.
3. A method according to claim 2 including continuously introducing the measured pressure into the simulation model, and
   continuously adapting characteristic impedance of the transmission line and windkessel compliance to the pressure of the windkessel compliance in accordance with the arctangent relation during each stroke.
4. A method according to claim 2 including linearizing the pressure on the basis of a linear pressure/volume relation of the aorta, and
   introducing said pressure into the model while maintaining the values of characteristic impedance of the transmission line and windkessel compliance associated with the final diastolic pressure.
5. A method according to claim 4 including calculating the flow q(t) according to a formula $q(t) = (1/Z_0) \cdot \{p(t) - p_w(t)\}$, where
$Z_0$ = characteristic $$\text{impedance} = \sqrt{(\rho/AC')} \ ,$$

and
$p_w$ = the compliance pressure, and
$\rho$ = density of blood,
$C'(p) = C_m/\{1 + (p-p_0)^{2/p_1^2}\}$,
where
$C_m = A_m/\pi p_1$ = the maximum compliance at $p = p_0$.
6. A method according to claim 1 including calculating cardiac output Q as product of the stroke volume and heart rate.
7. A method according to claim 6 including calculating a peripheral resistance $R_p$ in accordance with a formula $R_p = p_m/Q$, where $p_m$ = mean pressure = $(1/T) \cdot \int p(t)dt$, and calculating the flow through the peripheral resistance $R_p$ in accordance with a formula $Q_{Rp}(t) = p_0/R_p$.
8. A method according to claim 1 including measuring the blood pressure in the arteria radialis or brachialis, and filtering the measured pressure signal in order to correct resonance distortion in the pressure curve caused by transmission.
9. A method according to claim 1 including measuring the blood pressure, non-invasively, in the finger, and filtering the measured pressure signal in order to correct resonance distortion in the pressure curve caused by transmission.

* * * * *